United States Patent
Gotoh

(10) Patent No.: US 7,458,719 B2
(45) Date of Patent: Dec. 2, 2008

(54) X-RAY DIAGNOSTIC APPARATUS

(75) Inventor: Atsushi Gotoh, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/847,144

(22) Filed: Aug. 29, 2007

(65) Prior Publication Data
US 2007/0297574 A1 Dec. 27, 2007

Related U.S. Application Data

(62) Division of application No. 11/679,689, filed on Feb. 27, 2007, which is a division of application No. 11/364,208, filed on Mar. 1, 2006.

(30) Foreign Application Priority Data
Mar. 3, 2005 (JP) .............................. 2005-058741

(51) Int. Cl.
H05G 1/02 (2006.01)
(52) U.S. Cl. ...................................... 378/197; 378/195
(58) Field of Classification Search .......... 378/193–198
See application file for complete search history.

(56) References Cited

U.S. PATENT DOCUMENTS

| 4,922,512 | A | 5/1990 | Lajus et al. |
| 6,264,364 | B1 | 7/2001 | Pflaum et al. |
| 6,315,446 | B1 | 11/2001 | Kidd et al. |
| 6,325,537 | B1 | 12/2001 | Watanabe |
| 6,409,381 | B1 * | 6/2002 | Siebenhaar et al. ......... 378/197 |
| 2002/0131557 | A1 * | 9/2002 | Goto .......................... 378/154 |
| 2004/0081285 | A1 * | 4/2004 | Gotoh ......................... 378/193 |
| 2004/0170255 | A1 * | 9/2004 | Akutsu et al. ............... 378/197 |

FOREIGN PATENT DOCUMENTS

| JP | 8-71062 | 3/1996 |
| JP | 9-154836 | 6/1997 |
| JP | 2000-70248 | 3/2000 |
| JP | 2000-342639 A | 12/2000 |
| JP | 2003-250784 | 9/2003 |

* cited by examiner

*Primary Examiner*—Hoon Song
(74) *Attorney, Agent, or Firm*—Oblon, Spivak, McClelland, Maier & Neustadt, P.C.

(57) ABSTRACT

An X-ray diagnostic apparatus includes a floor rotating arm whose one end is mounted on a floor surface to be rotatable around a substantially vertical first rotation axis, a stand mounted on the other end of the floor rotating arm to be rotatable around a substantially vertical second rotation axis, an arm holder which is mounted on the stand so as to be rotatable around a substantially horizontal third rotation axis, a substantially C-shaped, C-arm which is mounted on the arm holder so as to be slidable/rotatable around a substantially horizontal fourth rotation axis, with an isocenter at which the fourth rotation axis intersects the third rotation axis being located on the first rotation axis when the C-arm is folded above the floor rotating arm, an X-ray generating unit mounted on one end of the C-arm, and an X-ray detecting unit mounted on the other end of the C-arm.

9 Claims, 9 Drawing Sheets

X-RAY DIAGNOSTIC APPARATUS

CROSS-REFERENCE TO RELATED APPLICATIONS

This application is a division of and claims the benefit of Priority under 37 C.F.R. 1.20 from U.S. application Ser. No. 11/679,689, filed Feb. 27, 2007, and is based upon and claims the benefit of priority from prior Japanese Patent Application No. 2005-058741, filed Mar. 3, 2005, the entire contents of which are incorporated herein by reference.

BACKGROUND OF THE INVENTION

1. Field of the Invention

The present invention relates to an X-ray diagnostic apparatus having a floor type C-arm.

2. Description of the Related Art

Medical image diagnostic techniques using X-ray diagnostic apparatuses, MRI apparatuses, and X-ray CT apparatuses have rapidly advanced with improvements in computer technology, and have become indispensable to current medical practice.

Recently, X-ray diagnosis has advanced mainly in the field of circulatory organs with improvements in catheter techniques. An X-ray diagnostic apparatus for the diagnosis of circulatory organs generally comprises an X-ray generating unit, an X-ray detecting unit, a holding apparatus which holds the X-ray generating unit and the X-ray detecting unit, a bed (top), a signal processing unit, a display unit, and the like. The holding apparatus allows X-ray imaging at an optimal position or in an optimal direction by pivoting, rotating, or moving a C-arm or Ω arm around a patient (to be referred to as a subject hereinafter).

As a detector used for the X-ray detecting unit of an X-ray diagnostic apparatus, an X-ray film or an I.I (Image Intensifier) has been used. In an X-ray imaging method using this I.I, X-ray projection data (to be referred to as projection data hereinafter) obtained when X-rays generated by the X-ray generating unit are transmitted through a subject is converted into an optical image by the I.I, and this optical image is displayed on a monitor after being converted into an electrical signal by an X-ray TV camera and A/D-converted. Therefore, the X-ray imaging method using the I.I allows real-time imaging which is impossible in the film system, and can acquire projection data in the form of digital signals. This makes it possible to perform various kinds of image processing. As a substitute to the above I.I, a flat panel detector comprising a two-dimensional array of detection elements has recently attracted attention. The replacement of such detectors is rapidly advanced.

FIG. 9 shows a C-arm holding apparatus used for a conventional circulatory organ X-ray diagnostic apparatus. An X-ray generating unit 1101 is mounted on one end (lower end) of a C-arm 1103 of a C-arm holding apparatus 1110, and an X-ray detecting unit 1102 comprising, for example, a flat panel detector is mounted on the other end (upper end) of the C-arm 1103 so as to face the X-ray generating unit 1101. A one-dot dashed line 1108 in FIG. 9 represents an imaging axis which connects the focal point of an X-ray tube in the X-ray generating unit 1101 to the center of the flat panel detector of the X-ray detecting unit 1102. The dot dashed line indicates a central line when a table top 1107 is at a lateral reference position, and a base line BL as a reference for an image posture which almost coincides with the body axis of the subject at the time of imaging operation.

The C-arm 1103 is held on a stand 1105, fixed on a floor surface 1106, through an arm holder 1104. The C-arm 1103 is mounted on an end portion of the arm holder 1104 so as to be slidable in the direction indicated by an arrow a. The arm holder 1104 is mounted on the upper portion of the stand 1105 so as to be pivotal or rotatable in the direction indicated by an arrow b.

The stand 1105 comprises a stand fixed portion 1105a fixed on the floor surface 1106 and a stand movable portion 1105b which can pivot about the column axis in the direction indicated by an arrow c.

The X-ray generating unit 1101 and X-ray detecting unit 1102 (to be collectively referred to as an imaging system hereinafter) are set at an optimal position in an optimal direction with respect to a subject (not shown) placed on the table top 1107 by sliding the C-arm 1103 in the direction a and pivoting the arm holder 1104 in the direction b. In addition, the imaging system and the C-arm 1103 can be retracted from the subject by pivoting the stand movable portion 1105b in the direction c. Retracting the imaging system and the C-arm 1103 makes it possible to ensure a working space around the jugular of the subject for a doctor or an examiner (to be referred to as an operator hereinafter) and facilitate replacement or repositioning of the subject on the table top 1107 before or after the examination, placement of anesthesia equipment, and the like.

Note that as the arm holder 1104 described above, an L-shaped offset arm is generally used as shown in FIG. 9. Making the arm holder 104 L-shaped allows the C-arm 1103 to be placed on a side of the table top 1107. This makes it possible to move an end portion of the table top 1107 in the longitudinal direction to near the stand 1105 in the direction indicated by an arrow d. That is, using the L-shaped arm holder 1104 makes it possible to widen the moving range of the table top 1107 and hence the imaging range with respect to the subject. In addition, the L shape of the arm holder 1104 has an advantage of being able to ensure a working space around the jugular of a subject for an operator.

However, the ensurance of a working space or the widening of the imaging range by pivoting the stand movable portion 1105b or using the L-shaped arm holder 1104 has its own limit because the stand 1105 is fixed on the floor surface 1106, and hence is not necessarily sufficient for the operator.

In order to solve such problems, a method has been proposed in which a ceiling-mounted C-arm holding apparatus having an arm whose one end is pivotally mounted on the ceiling and an arm holder mounted on the other end of the arm is used, and an imaging region of a subject can be arbitrarily set by aligning the position of the pivot axis of the arm with the central line of a table top in the longitudinal direction (see Jpn. Pat. Appln. KOKAI Publication No. 2000-70248).

BRIEF SUMMARY OF THE INVENTION

It is an object of the present invention to widen a working space and increase the degree of freedom of imaging in an X-ray diagnostic apparatus having a floor type C-arm.

According to a first aspect of the present invention, there is provided an X-ray diagnostic apparatus comprising a floor rotating arm whose one end is mounted on a floor surface so as to be rotatable around a substantially vertical first rotation axis, a stand which is mounted on the other end of the floor rotating arm so as to be rotatable around a substantially vertical second rotation axis, an arm holder which is mounted on the stand so as to be rotatable around a substantially horizontal third rotation axis, a substantially C-shaped, C-arm which is mounted on the arm holder so as to be slidable/rotatable around a substantially horizontal fourth rotation axis, with an isocenter at which the fourth rotation axis intersects the third rotation axis being located on the first rotation axis when the C-arm is located immediately above the floor rotating arm, an X-ray generating unit mounted on one end of the C-arm, and an X-ray detecting unit mounted on the other end of the C-arm.

According to a second aspect of the present invention, there is provided an X-ray diagnostic apparatus comprising a floor rotating arm whose one end is mounted on a floor surface so as to be rotatable around a substantially vertical first rotation axis, a stand which is supported on the other end of the floor rotating arm so as to be rotatable around a substantially vertical second rotation axis, an arm holder which is supported on the stand so as to be rotatable around a substantially horizontal third rotation axis, a substantially C-shaped, C-arm which is supported on the arm holder so as to be slidable/rotatable around a substantially horizontal fourth rotation axis, with an isocenter at which the third rotation axis intersects the fourth rotation axis being located on an arcuated path intersecting the first rotation axis upon rotation of the stand, an X-ray generating unit mounted on one end of the C-arm, and an X-ray detecting unit mounted on the other end of the C-arm.

According to a third aspect of the present invention, there is provided an X-ray diagnostic apparatus comprising a floor rotating arm whose one end is mounted on a floor surface so as to be rotatable around a substantially vertical first rotation axis, a stand which is supported on the other end of the floor rotating arm so as to be rotatable around a substantially vertical second rotation axis, an arm holder which is supported on the stand so as to be rotatable around a substantially horizontal third rotation axis, a substantially C-shaped, C-arm which is supported on the arm holder so as to be slidable/rotatable around a substantially horizontal fourth rotation axis, with a distance between the first rotation axis and the second rotation axis being substantially equal to a distance from an isocenter at which the third rotation axis intersects the fourth rotation axis to the second rotation axis, an X-ray generating unit mounted on one end of the C-arm, and an X-ray detecting unit mounted on the other end of the C-arm.

According to a fourth aspect of the present invention, there is provided an X-ray diagnostic apparatus comprising a floor rotating arm whose one end is mounted on a floor surface so as to be rotatable around a substantially vertical first rotation axis, a stand which is supported on the other end of the floor rotating arm so as to be rotatable around a substantially vertical second rotation axis, an arm holder which is supported on the stand so as to be rotatable around a substantially horizontal third rotation axis, a substantially C-shaped, C-arm which is supported on the arm holder so as to be slidable/rotatable around a substantially horizontal fourth rotation axis, with an imaging axis passing through an X-ray focal point of the X-ray generating unit and the center of a detection surface of the X-ray detecting unit substantially coinciding with the first rotation axis when the stand, the arm holder, and the C-arm are located at standard positions, an X-ray generating unit mounted on one end of the C-arm, and an X-ray detecting unit mounted on the other end of the C-arm.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below with reference to the views of the accompanying drawing.

Figure 1A:
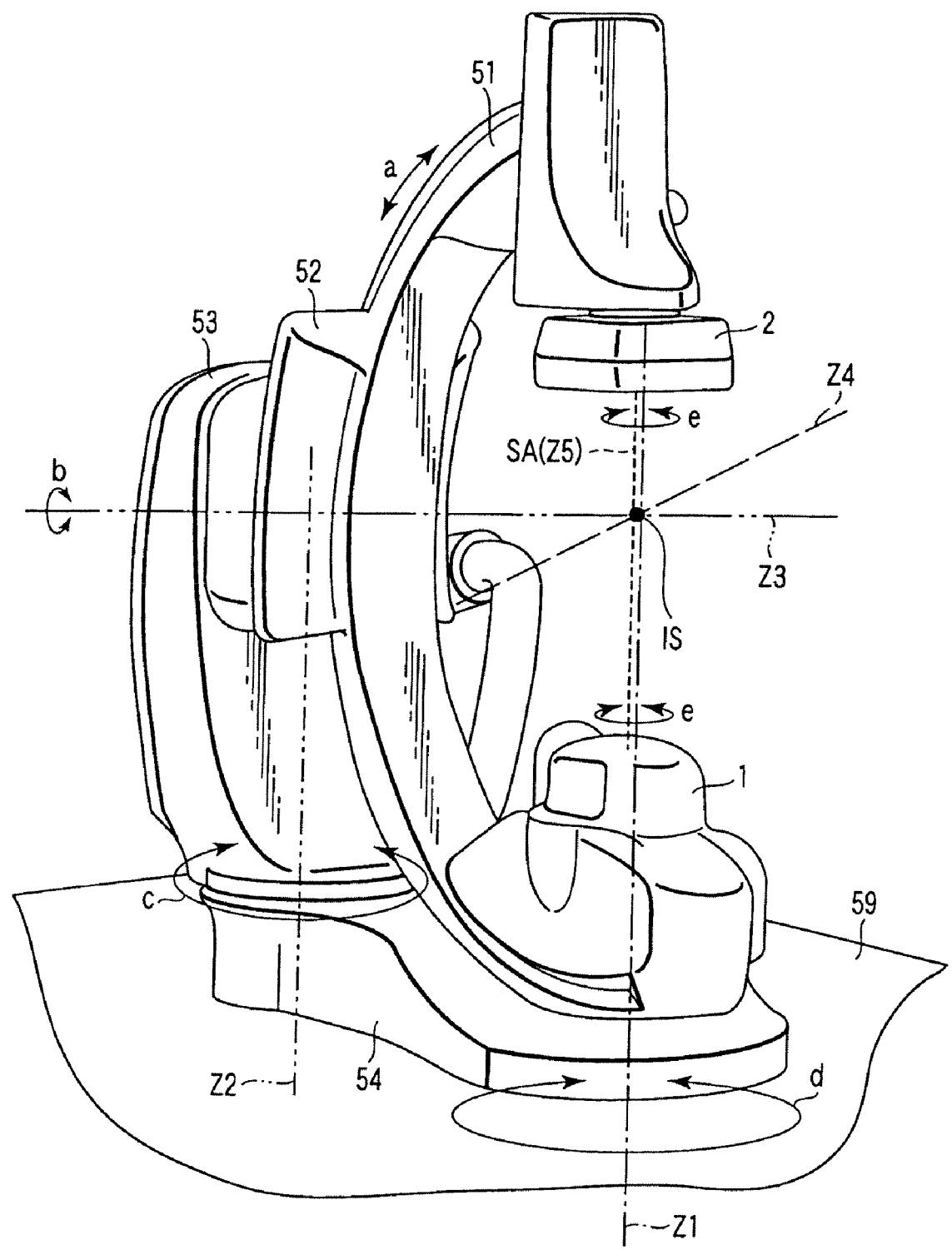
FIG. 1A is a perspective view of an X-ray diagnostic apparatus according to an embodiment of the present invention.
Figure 1B:
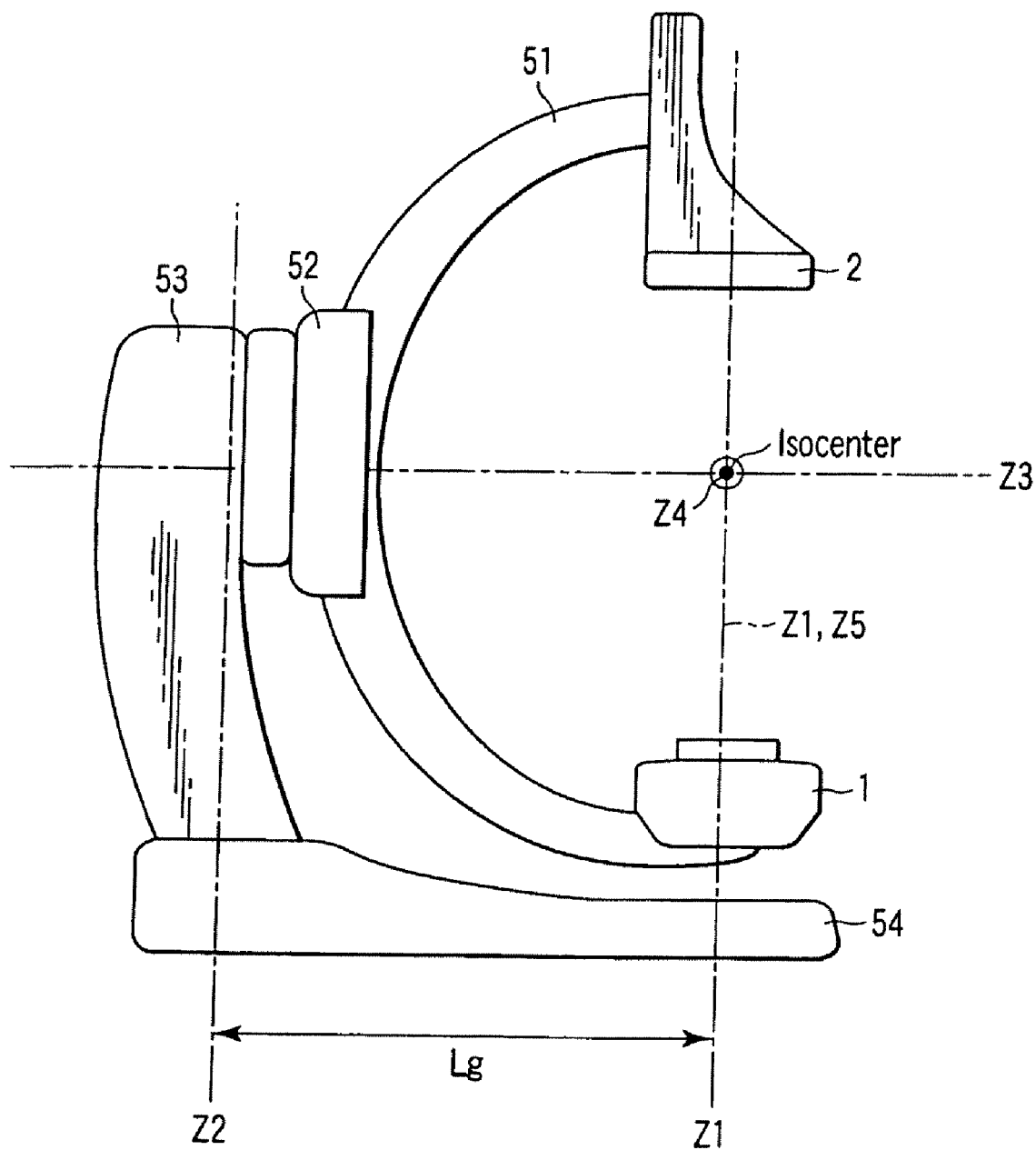
FIG. 1B is a side view of the X-ray diagnostic apparatus in FIG. 1A.
Figure 2:
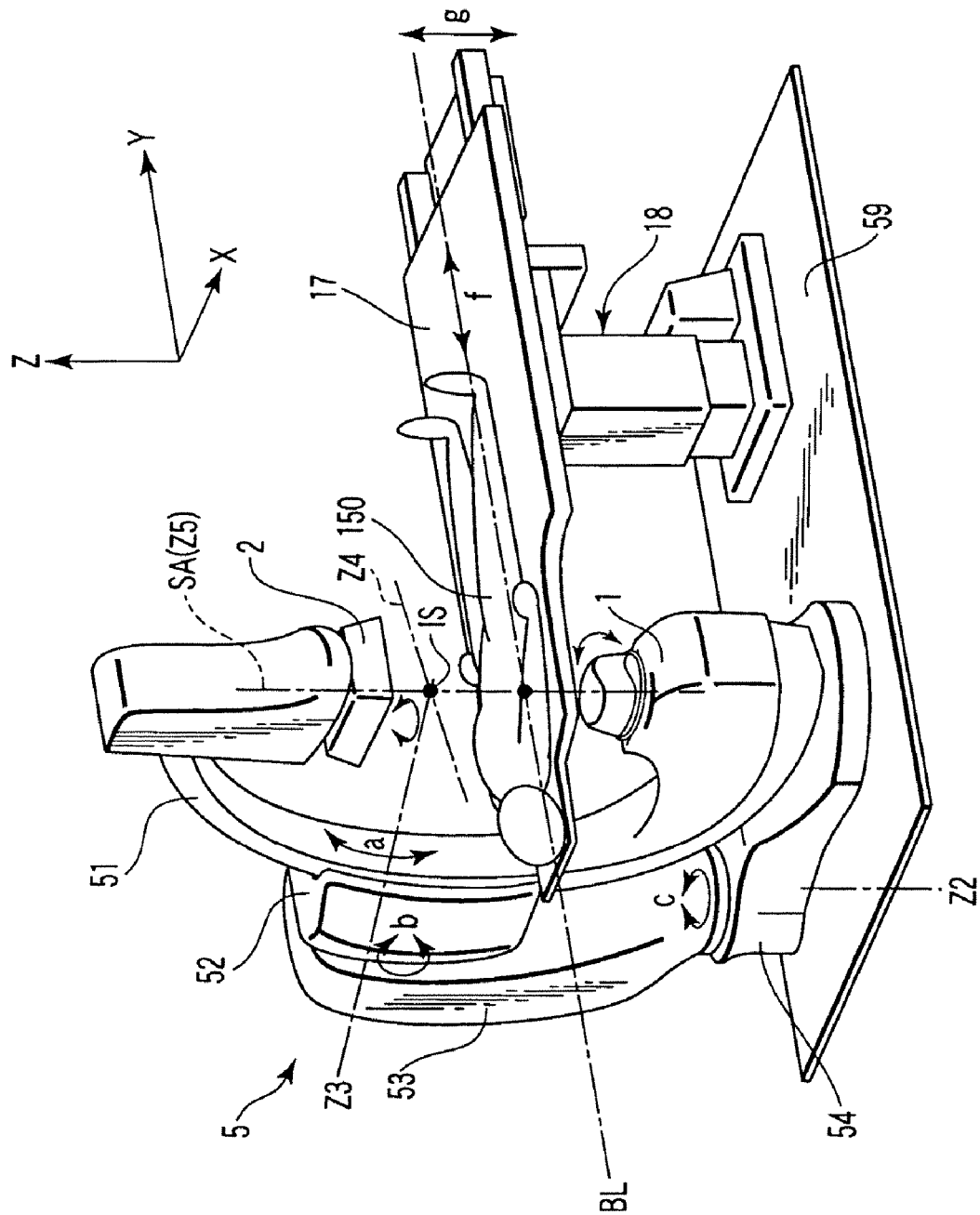
FIG. 2 is a perspective view of a C-arm holding apparatus for the X-ray diagnostic apparatus according to the embodiment of the present invention.

As shown in FIGS. 1A, 1B, and 2, a floor rotating arm 54 is provided on a floor surface 59 so as to be rotatable (d) around a substantially vertical first rotation axis Z1 at one end of the arm. Note that the first rotation axis Z1 is defined as an actual rotation central axis in terms of rotational motion instead of a rotation axis in terms of structure. Obviously, the actual rotation central axis in term of rotational motion may or may not coincide with rotation axis in terms of structure. This also applies to rotation axes Z2, Z3, Z4, and Z5 to be described later.

The first rotation axis Z1 of the floor rotating arm 54 intersects a base line BL which nearly coincides with the central line of a table top 17. Note that the base line BL nearly coincides with the body axis of a subject 150 at the time of imaging operation. The table top 17 is provided on a bed 18 so as to be movable along the base line BL.

A stand 53 is supported on the other end of the floor rotating arm 54 so as to be rotatable (c) around the substantially vertical second rotation axis Z2. An arm holder 52 is supported on the stand 53 so as to be rotatable (b) around the substantially horizontal third rotation axis (C-arm rotation axis). A substantially C-arm 51 is supported on the arm holder 52 so as to be slidable (a) around the substantially horizontal fourth rotation axis (slide rotation axis) Z4 perpendicular to the C-arm rotation axis Z3. An X-ray collimating unit 1 is mounted on one end of the C-arm 51, and an X-ray detecting unit (commonly named a flat panel detector (FPD)) 2 typically having a two-dimensional array of X-ray detection semiconductor elements is mounted on the other end of the C-arm 51.

Figure 5A:
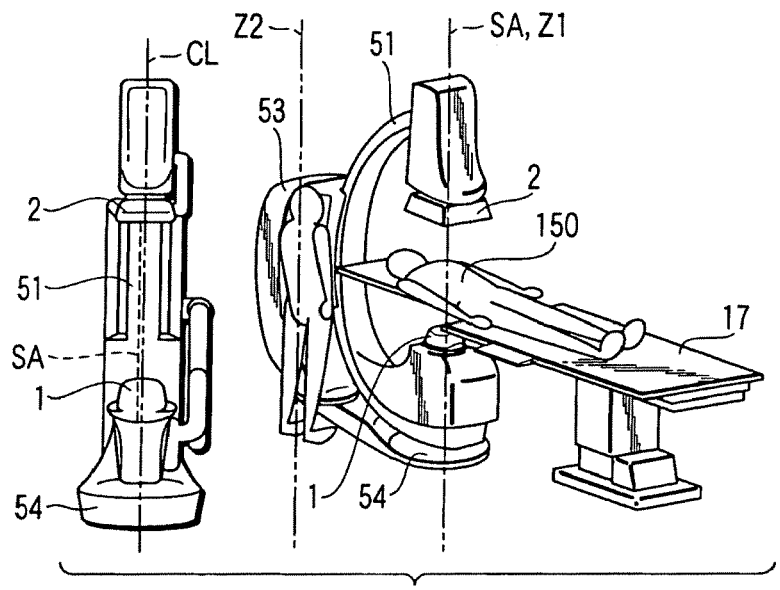
FIG. 5A is a view showing a jugular portion approach position subjected to posture control by a moving mechanism driving control unit in FIG. 3.

The C-arm 51 is provided in a zero offset state. That is, when the C-arm 51 is at a standard angle, it is located immediately above the floor rotating arm 54. More specifically, as shown in FIG. 5A, when viewed from the front side, the C-arm 51 is provided in a zero offset state such that a central line CL of the C-arm 51 coincides with rotation axes Z1 and Z5.

Although not shown, the X-ray generating unit 1 has an X-ray tube and an X-ray collimating mechanism which forms an X-ray irradiation field into an arbitrary shape such as a rectangular shape or a circular shape. The X-ray collimating mechanism is supported on collimator and detector mechanism 515-1 (see FIG. 3) so as to be axially rotatable around an imaging axis SA (coinciding with the fifth rotation axis Z5) connecting the X-ray focal point of the X-ray tube to the center of the detection surface of the X-ray detecting unit 2. Likewise, the X-ray detecting unit 2 is supported on a FPD rotation mechanism 515-2 so as to be axially rotatable around the imaging axis SA (the fifth rotation axis Z5).

The imaging axis SA (Z5) passing through the X-ray focal point of the X-ray generating unit 1 and the center of the detection surface of the X-ray detecting unit 2 is designed to intersect the C-arm horizontal rotation axis Z3 and the slide rotation axis Z4 at one point. As is known, the absolute coordinates of the intersection (a position on the imaging room coordinate system) do not move even when the C-arm 51 rotates around the C-arm rotation axis Z3 and rotates around the slide rotation axis Z4 and the floor rotating arm 54 rotates around the first rotation axis Z1 as long as the stand 53 does not rotate around the second rotation axis Z2, and is generally called an isocenter.

As shown in FIGS. 1A and 1B, when the rotational angle of the stand 53 around the second rotation axis Z2 is set at a standard angle (0°) and the C-arm 51 is located immediately above the floor rotating arm 54 so as to overlap it, the isocenter is located on the first rotation axis Z1 of the floor rotating arm 54. In other words, when the rotational angle of the stand 53 around the second rotation axis Z2 is set at the standard angle (0°) and the C-arm 51 is located above the floor rotating arm 54 so as to overlap it, the imaging axis SA (Z5), the C-arm horizontal rotation axis Z3, the slide rotation axis Z4, and the first rotation axis Z1 of the floor rotating arm 54 intersect the isocenter at one point. That is, the length of the floor rotating arm 54, the size of the stand 53, the size of the arm holder 52, and the radius of the C-arm 51 are designed such that the distance (shortest processing) between the first rotation axis Z1 of the floor rotating arm 54 and the second rotation axis Z2 of the stand 53 becomes equal to the distance (shortest processing) between the second rotation axis Z2 of the stand 53 and the isocenter IS.

Assume that the rotational angle of the C-arm 51 around the C-arm horizontal rotation axis Z3 is at the standard angle (0°), and the rotational angle of the C-arm 51 around the slide rotation axis Z4 is at the standard angle (0°) to set the imaging axis SA (Z5) in the vertical direction. According to the above designs, in this case, when the rotational angle of the stand 53 around the second rotation axis Z2 is at the standard angle (0°), the imaging axis SA (Z5) substantially coincides with the first rotation axis Z1 of the floor rotating arm 54.

Figure 3:
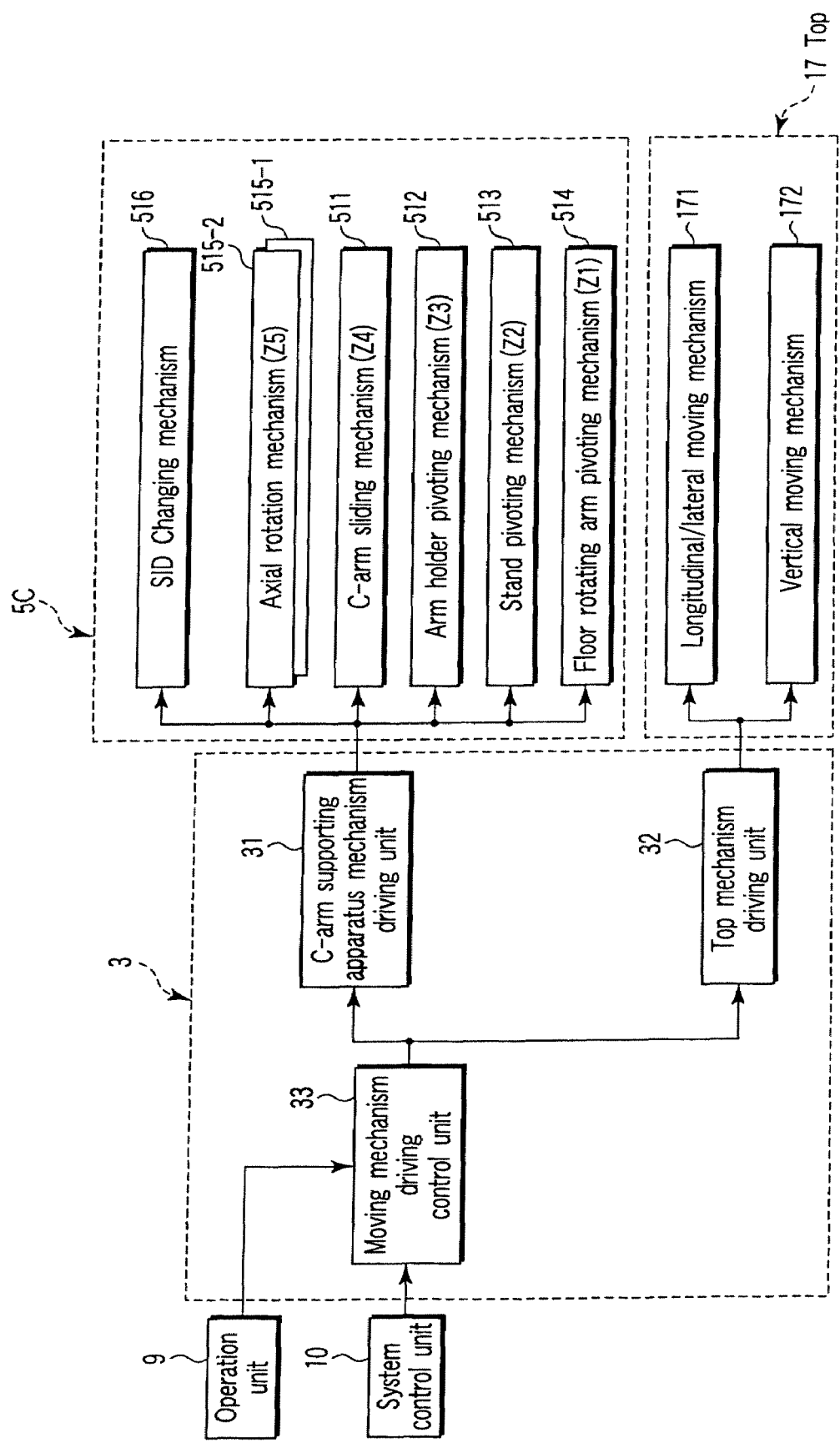
FIG. 3 is a functional block diagram of the main part of the X-ray diagnostic apparatus according to the embodiment of the present invention.

As shown in FIG. 3, driving signals are supplied from a C-arm holding apparatus mechanism driving unit 31 to mechanisms 511, 512, 513, 514, the mechanisms 515-1 and 515-2, and a mechanism 516 of the C-arm holding apparatus 5 under the control of a moving mechanism driving control unit 33 of a moving mechanism driving unit 3 on the basis of control signals from a system control unit 10 or operation signals from an operation unit 9. With this operation, the respective portions rotate and slide. Likewise, driving signals are supplied from a catheterization table mechanism driving unit 32 to a longitudinal/lateral moving mechanism 171 and vertical moving mechanism 172 of the table top 17 under the control of the moving mechanism driving control unit 33 of the moving mechanism driving unit 3 on the basis of control signals from the system control unit 10 or operation signals from the operation unit 9. With this operation, the table top 17 is set in a brake-released state, and can move in a longitudinal direction f (Y direction) or a lateral direction (X direction). Alternatively, the table top 17 is controlled to move in an up-and-down direction g.

Figure 4:
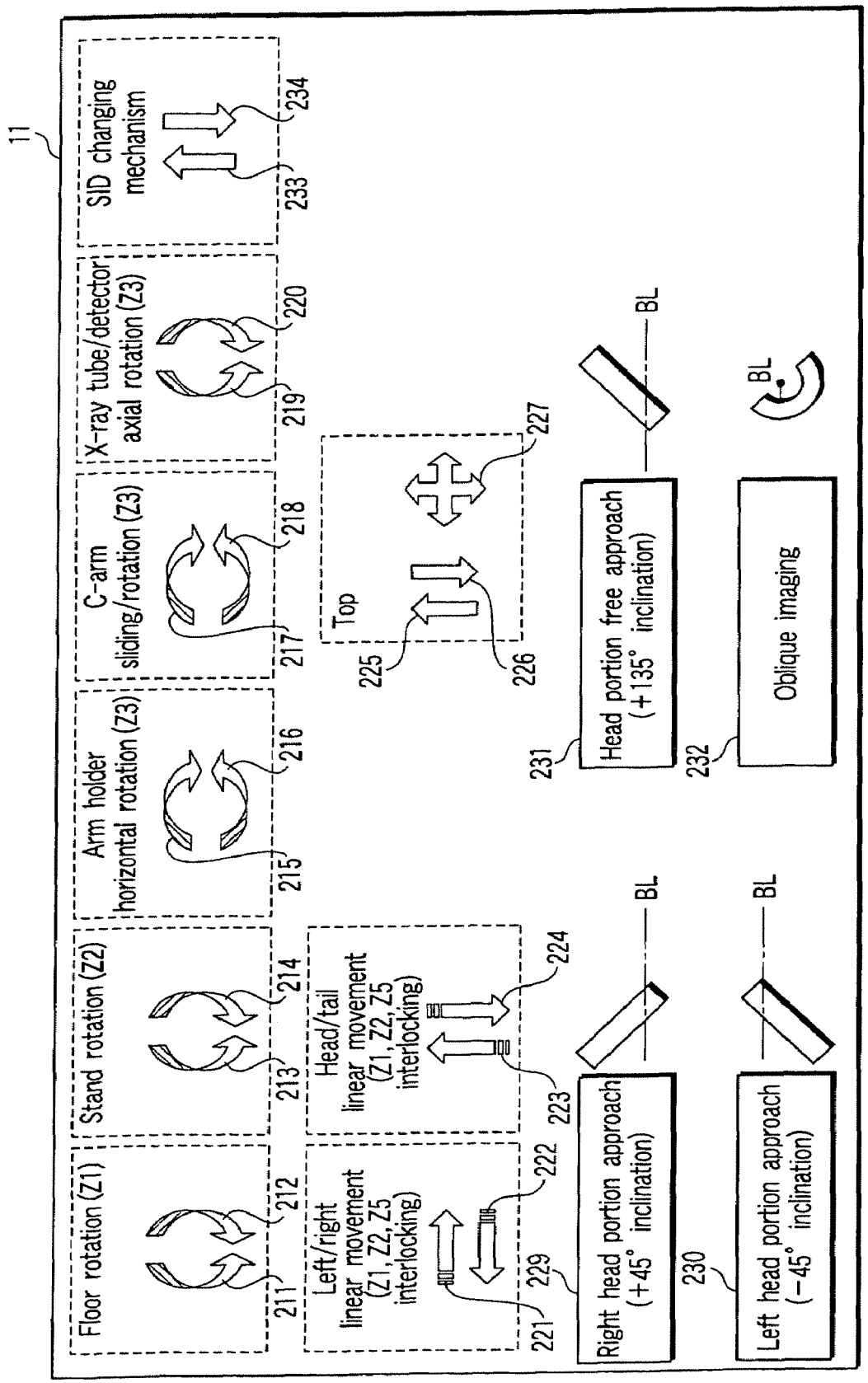
FIG. 4 is a view showing an example of the operation surface of an operation unit in FIG. 3.

FIG. 4 shows the operation surface of an operation unit 11. The operation surface is implemented by either a touch panel screen or a console on which real switches and buttons are arranged. The operation surface is provided with manual operation buttons 211 to 227, 233, and 234 for manually operating the movement of the respective portions. The operation surface is also provided with preset buttons 229, 230, 231, and 232 for automatically moving the C-arm holding apparatus 5 to predetermined postures.

When the floor rotating button 211 is clicked or pressed, the control unit 33 controls the moving unit 31 such that the floor rotating arm 54 is rotated forward (counterclockwise) around the rotation axis Z1 by the floor rotating arm pivoting mechanism 514 by a corresponding operation amount, typically an angle corresponding to the time during which the button is pressed. When the floor rotating button 212 is clicked or pressed, the control unit 33 controls the driving unit 31 such that the floor rotating arm 54 is rotated backward (clockwise) around the rotation axis Z1 by the floor rotating arm pivoting mechanism 514 by an angle corresponding to the operation amount.

When the stand rotating button 213 is clicked or pressed, the control unit 33 controls the driving unit 31 such that the stand 53 is rotated forward (counterclockwise) around the rotation axis Z2 by the stand pivoting mechanism 513 by an angle corresponding to the operation amount. When the stand rotating button 214 is clicked or pressed, the control unit 33 controls the driving unit 31 such that the stand 53 is rotated backward (clockwise) around the rotation axis Z2 by the stand pivoting mechanism 513 by an angle corresponding to the operation amount.

When the C-arm rotating button 215 is clicked or pressed, the control unit 33 controls the driving unit 31 such that the arm holder 52 is horizontally rotated forward around the rotation axis Z3 by the C-arm rotating mechanism 512 by an angle corresponding to the operation amount. When the C-arm rotating button 216 is clicked or pressed, the control unit 33 controls the driving unit 31 such that the arm holder 52 is horizontally rotated backward around the rotation axis Z3 by the C-arm rotating mechanism 512 by an angle corresponding to the operation amount.

When the C-arm sliding button 217 is clicked or pressed, the control unit 33 controls the driving unit 31 such that the C-arm 51 is slid forward around the rotation axis Z4 along the arm holder 52 by the C-arm sliding mechanism 511 by an angle corresponding to the operation amount. When the C-arm sliding button 218 is clicked or pressed, the control unit 33 controls the driving unit 31 such that the C-arm 51 is slid backward around the rotation axis Z4 along the arm holder 52 by the C-arm sliding mechanism 511 by an angle corresponding to the operation amount.

When the collimator/detector axis rotating button 219 is clicked or pressed, the control unit 33 controls the driving unit 31 such that the X-ray collimating device is axially rotated, together with the X-ray detecting unit 2, in synchronism witch each other, forward around the rotation axis Z5 (imaging axis SA) by the axial rotation mechanisms 515-1 and 515-2 by an angle corresponding to the operation amount. When the X-ray tube/detector axis rotating button 220 is clicked or pressed, the control unit 33 controls the driving unit 31 such that the X-ray stop device is axially rotated, together with the X-ray detecting unit 2, in synchronism witch each other, backward around the rotation axis Z5 (imaging axis SA) by the axial rotation mechanisms 515-1 and 515-2 by an angle corresponding to the operation amount.

When the table top elevating button 225 is clicked or pressed, the control unit 33 controls the driving unit 32 such that the table top 17 is elevated upward along a vertical axis by the vertical moving mechanism 172 by a distance corresponding to the operation amount. When the table top elevating button 226 is clicked or pressed, the control unit 33 controls the driving unit 32 such that the table top 17 is elevated downward along a vertical axis by the vertical moving mechanism 172 by a distance corresponding to the operation amount. When the table top brake button 227 is clicked or pressed, the brake is released, and the table top 17 can move in the longitudinal direction (Y direction) or in the lateral direction (X direction). If the table top brake button 227 is clicked or pressed again after the table top is moved, the brake is applied.

When the SID changing button 233 is clicked or pressed, the control unit 33 controls the SID changing mechanism 516 to move the X-ray detecting unit 2 away from the isocenter IS along the imaging axis SA by a distance corresponding to the operation amount so as to increase the SID (X-ray tube/X-ray detector distance). When the SID changing button 234 is clicked or pressed, the control unit 33 controls the SID changing mechanism 516 to move the X-ray detecting unit 2 close to the isocenter IS along the imaging axis SA by a distance corresponding to the operation amount so as to decrease the SID (X-ray tube/X-ray detector distance).

Figure 7A:
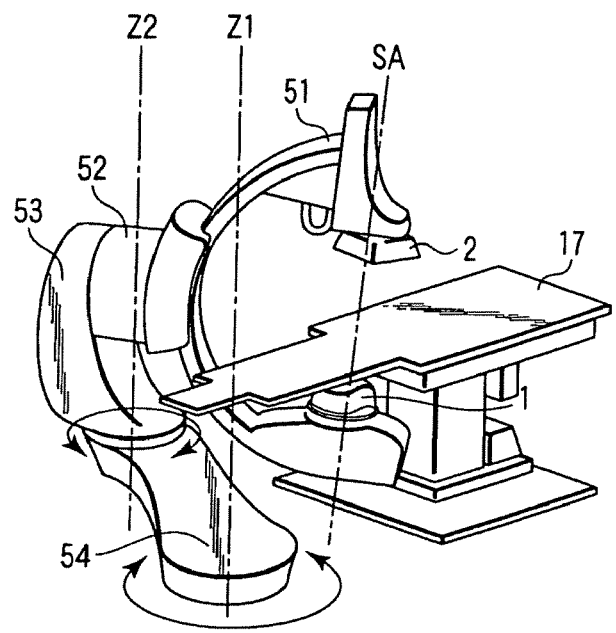
FIG. 7A is a perspective view showing left/right linear movement and jugular/tail linear movement realized by interlocking control by the moving mechanism driving control unit in FIG. 3.
Figure 7B:
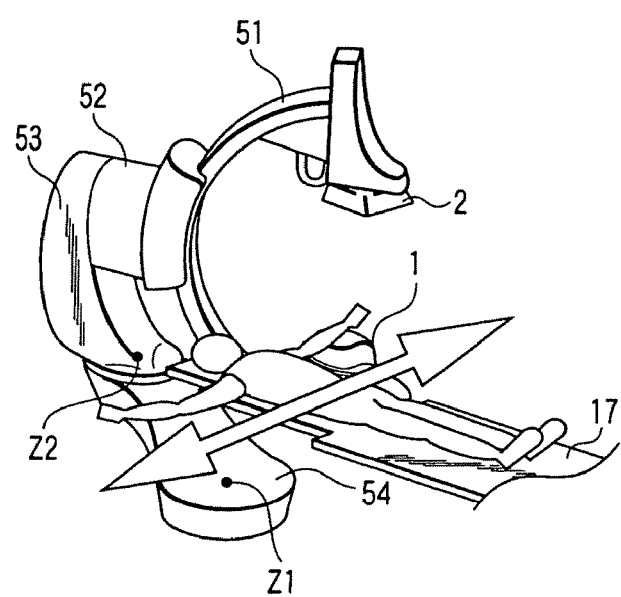
FIG. 7B is a perspective view showing the left/right linear movement of the imaging axis which is realized by interlocking control by the moving mechanism driving control unit in FIG. 3.

When the left/right linear movement button 221 is clicked or pressed, the control unit 33 controls the driving unit 31 to move the imaging axis SA to the left along a straight line which passes through the initial position shown in FIG. 7A and is perpendicular to the base line BL by a distance corresponding to the operation amount (see FIG. 7B). In order to linearly move the imaging axis SA, the control unit 33 interlocks the rotation of the floor rotating arm 54 around the rotation axis Z1 with the rotation of the stand 53 around the rotation axis Z2. In addition, the control unit 33 interlocks the rotation of the X-ray collimating device and X-ray detection unit around the rotation axis Z5 (imaging axis SA) by the collimator/detector rotation mechanisms 515-1 and 515-2 with the rotation of the floor rotating arm 54 around the rotation axis Z1 and the rotation of the stand 53 around the rotation axis Z2 to fix the direction of an image by preventing the rotation of the direction of the image upon the rotation of the floor rotating arm 54 around the rotation axis Z1 and the rotation of the stand 53 around the rotation axis Z2.

Likewise, when the left/right linear movement button 222 is clicked or pressed, the control unit 33 controls the driving unit 31 to move the imaging axis SA to the right along a straight line which passes through the initial position shown in FIG. 7A and is perpendicular to the base line BL by a distance corresponding to the operation amount (see FIG. 7B). In order to linearly move the imaging axis SA, the control unit 33 interlocks the rotation of the floor rotating arm 54 around the rotation axis Z1 with the rotation of the stand 53 around the rotation axis Z2. In addition, the control unit 33 interlocks the rotation of the X-ray collimating device and X-ray detection unit around the rotation axis Z5 (imaging axis SA) by the collimator/detector rotation mechanisms 515-1 and 515-2 with the rotation of the floor rotating arm 54 around the rotation axis Z1 and the rotation of the stand 53 around the rotation axis Z2 to fix the direction of an image by preventing the rotation of the direction of the image upon the rotation of the floor rotating arm 54 around the rotation axis Z1 and the rotation of the stand 53 around the rotation axis Z2.

Figure 7C:
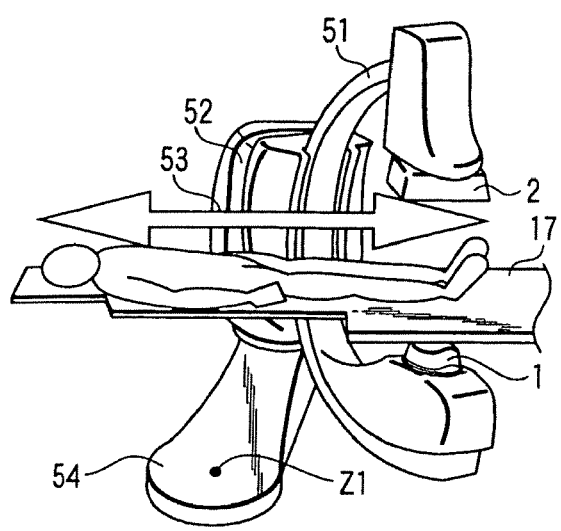
FIG. 7C is a perspective view showing the jugular/tail linear movement of the imaging axis which is realized by interlocking control by the moving mechanism driving control unit in FIG. 3.

When the jugular/tail linear movement button 223 is clicked or pressed, the control unit 33 controls the driving unit 31 to move the imaging axis SA to the jugular side along the base line BL by a distance corresponding to the operation amount (see FIG. 7C). In order to linearly move the imaging axis SA, the control unit 33 interlocks the rotation of the floor rotating arm 54 around the rotation axis Z1 with the rotation of the stand 53 around the rotation axis Z2. In addition, the control unit 33 interlocks the rotation of the X-ray collimating device and X-ray detection unit around the rotation axis Z5 (imaging axis SA) by the collimator/detector rotation mechanisms 515-1 and 515-2 with the rotation of the floor rotating arm 54 around the rotation axis Z1 and the rotation of the stand 53 around the rotation axis Z2 to fix the direction of an image by preventing the rotation of the direction of the image upon the rotation of the floor rotating arm 54 around the rotation axis Z1 and the rotation of the stand 53 around the rotation axis Z2.

When the jugular/tail linear movement button 224 is clicked or pressed, the control unit 33 controls the driving unit 31 to move the imaging axis SA to the leg side along the base line BL by a distance corresponding to the operation amount (see FIG. 7C). In order to linearly move the imaging axis SA, the control unit 33 interlocks the rotation of the floor rotating arm 54 around the rotation axis Z1 with the rotation of the stand 53 around the rotation axis Z2. In addition, the control unit 33 interlocks the rotation of the X-ray collimating device and X-ray detection unit around the rotation axis Z5 (imaging axis SA) by the collimator/detector rotation mechanisms 515-1 and 515-2 with the rotation of the floor rotating arm 54 around the rotation axis Z1 and the rotation of the stand 53 around the rotation axis Z2 to fix the direction of an image by preventing the rotation of the direction of the image upon the rotation of the floor rotating arm 54 around the rotation axis Z1 and the rotation of the stand 53 around the rotation axis Z2.

Figure 5B:
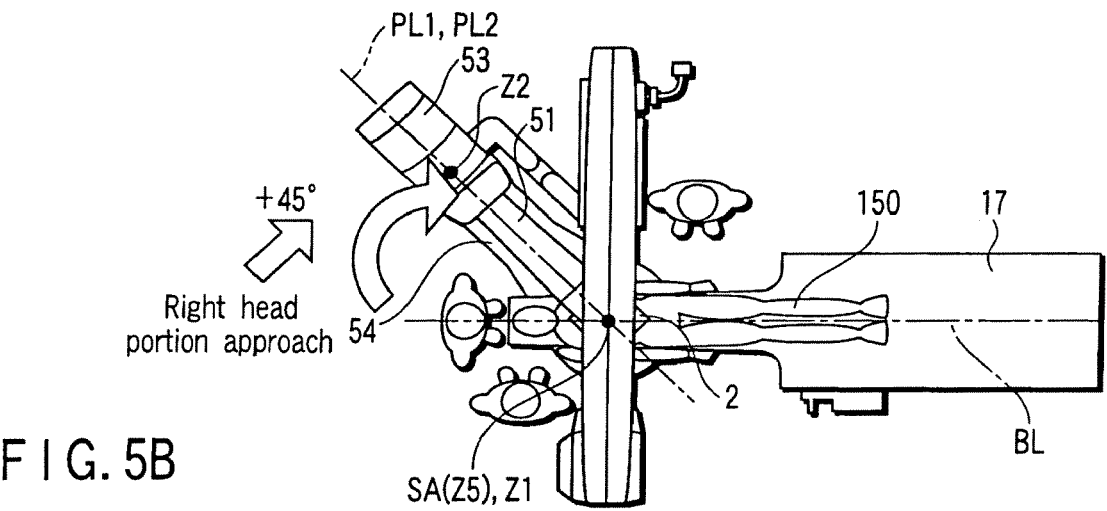
FIG. 5B is a view showing a right jugular portion approach position subjected to posture control by the moving mechanism driving control unit in FIG. 3.

When the right jugular portion approach position button 229 is clicked or pressed, as shown in FIG. 5B, the control unit 33 controls the driving unit 31 to set the C-arm holding apparatus 5 in a preset posture (position) suitable for enlarging a work space for allowing an operator to approach the subject 150 from the right jugular side. More specifically, when the stand 53 rotates to the reference position, the C-arm 51 overlaps above the floor rotating arm 54. That is, a second posture line PL2 connecting the second rotation axis Z2 to the fifth rotation axis Z5 (imaging axis SA) coincides with a first posture line PL1 connecting the first rotation axis Z1 to the second rotation axis Z2. This makes the fifth rotation axis Z5 (imaging axis SA) of the X-ray collimating and X-ray detecting unit 2 almost coincide with the first rotation axis Z1 of the floor rotating arm 54. In addition, the first and second posture lines PL1 and PL2 inline to the positive side at almost 45° with respect to the base line BL. The control unit 33 controls the driving unit 31 to control the rotation of the floor rotating arm 54 around the first rotation axis Z1 while the position of the stand 53 around the second rotation axis Z2 is in a zero-degree state, thereby placing the C-arm holding apparatus 5 in such a preset posture. Setting such a posture makes it possible to ensure a work space large enough for the operator to approach the right jugular portion of the subject 150. In addition, since this posture is automatically set by the operation of the right jugular portion approach position button 229, the C-arm holding apparatus 5 can quickly shift to the posture. The inclination angle is finely adjusted by manually operating the buttons 211 and 212, as needed. Note that the control unit 33 performs control to correct the direction of an image in accordance with the rotation of the X-ray detecting unit 2 (FPD) or X-ray collimating device. In addition, the preset angle can be changed by setting, as needed.

Figure 5C:
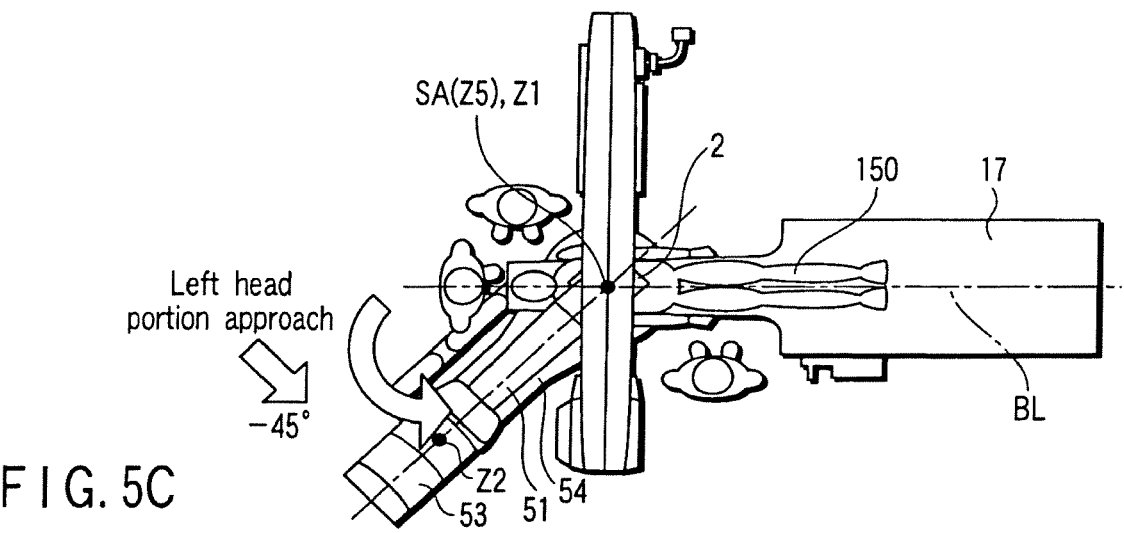
FIG. 5C is a view showing a left jugular portion approach position subjected to posture control by the moving mechanism driving control unit in FIG. 3.

When the left jugular portion approach position button 230 is clicked or pressed, as shown in FIG. 5C, the control unit 33 controls the driving unit 31 to set the C-arm holding apparatus 5 in a preset posture (position) suitable for enlarging a work space for allowing the operator to approach the subject 150 from the left jugular side. More specifically, as in the case of the right jugular portion approach position, the C-arm 51 overlaps above the floor rotating arm 54. In addition, the first and second posture lines PL1 and PL2 inline to the negative side at almost 45° with respect to the base line BL. The control unit 33 controls the driving unit 31 to control the rotation of the floor rotating arm 54 around the first rotation axis Z1 while the position of the stand 53 around the second rotation axis Z2 is in a zero-degree state, thereby placing the C-arm holding apparatus 5 in such a preset posture. Setting such a posture makes it possible to ensure a work space large enough for the operator to approach the left jugular portion of the subject 150. In addition, since this posture is automatically set by the operation of the left jugular portion approach position button 230, the C-arm holding apparatus 5 can quickly shift to the posture. The inclination angle is finely adjusted by manually operating the buttons 211 and 212, as needed. Note that the control unit 33 performs control to correct the direction of an image in accordance with the rotation of the X-ray detecting unit 2 (FPD) or X-ray collimating device. In addition, the preset angle can be changed by setting, as needed.

Figure 6A:
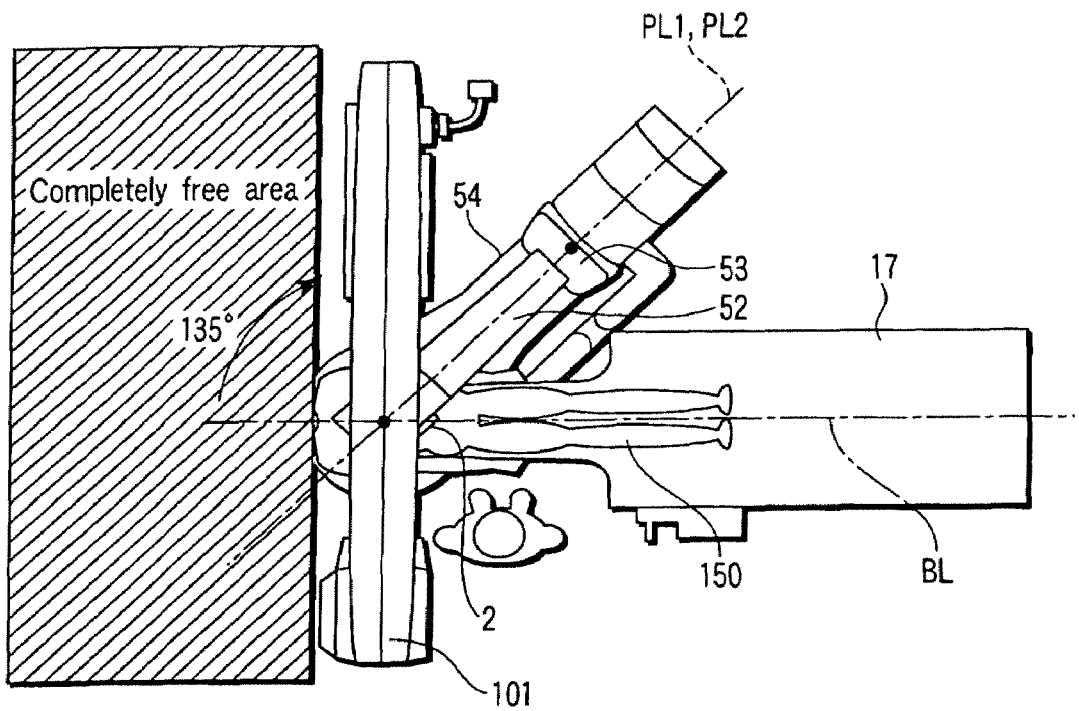
FIG. 6A is a view showing a jugular portion free approach position subjected to posture control by the moving mechanism driving control unit in FIG. 3.
Figure 6B:
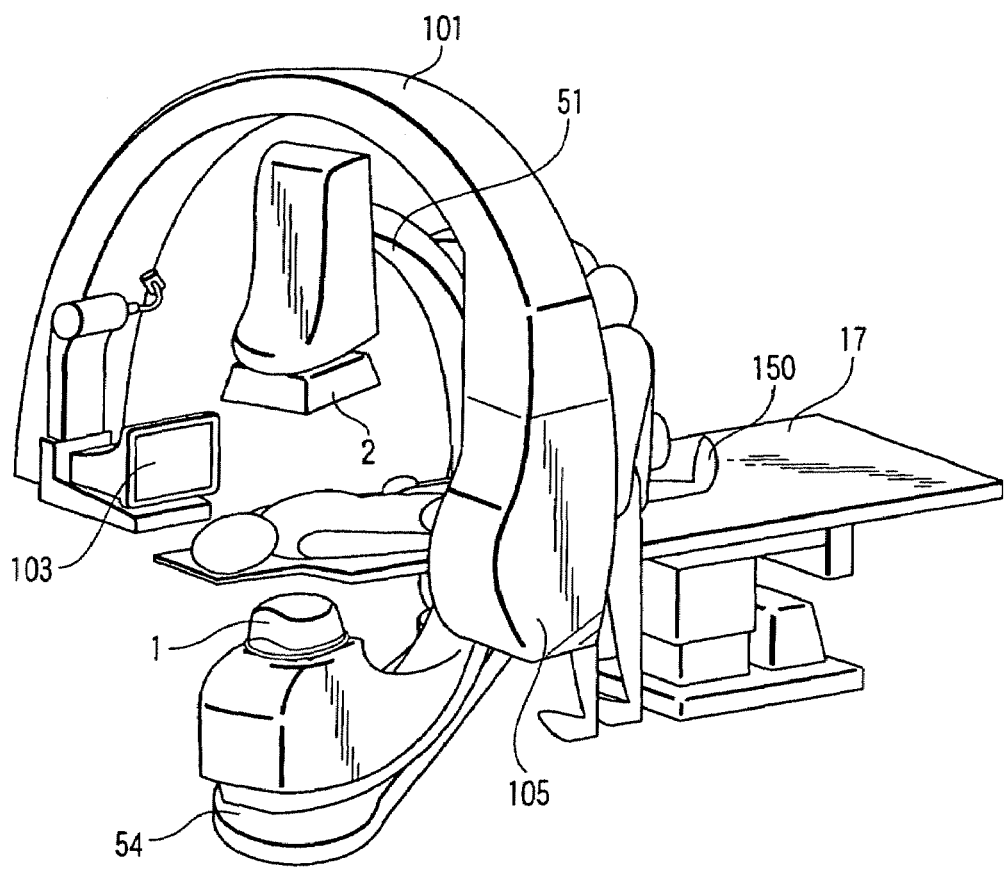
FIG. 6B is a perspective view of the apparatus shown in FIG. 6A.

When the jugular portion free approach position button 231 is clicked or pressed, as shown in FIGS. 6A and 6B, the control unit 33 controls the driving unit 31 to set the C-arm holding apparatus 5 in a preset posture (position) suitable for enlarging a work space for allowing the operator to approach the subject 150 from the entire jugular region. The posture by which a work space is ensured for this entire jugular region is typically effective for biplane imaging operation using a ceiling-mounted Ω arm 101 having an X-ray generating unit 105 and an X-ray detecting unit 103 mounted on the two ends in the horizontal direction.

More specifically, as in the case of the right jugular portion approach position, the C-arm 51 overlaps above the floor rotating arm 54. In addition, the first and second posture lines PL1 and PL2 inline to the positive or negative side at almost 135° with respect to the base line BL. The control unit 33 controls the driving unit 31 to control the rotation of the floor rotating arm 54 around the first rotation axis Z1 while the position of the stand 53 around the second rotation axis Z2 is in a zero-degree state, thereby placing the C-arm holding apparatus 5 in such a preset posture. Setting such a posture makes it possible to ensure a work space large enough for the operator to approach the jugular portion of the subject 150. In addition, since this posture is automatically set by the operation of the jugular portion free approach position button 231, the C-arm holding apparatus 5 can quickly shift to the posture. The inclination angle is finely adjusted by manually operating the buttons 211 and 212, as needed. Note that the control unit 33 performs control to correct the direction of an image in accordance with the rotation of the X-ray detecting unit 2 (FPD) or X-ray collimating device. In addition, the preset angle can be changed by setting, as needed.

Figure 8:
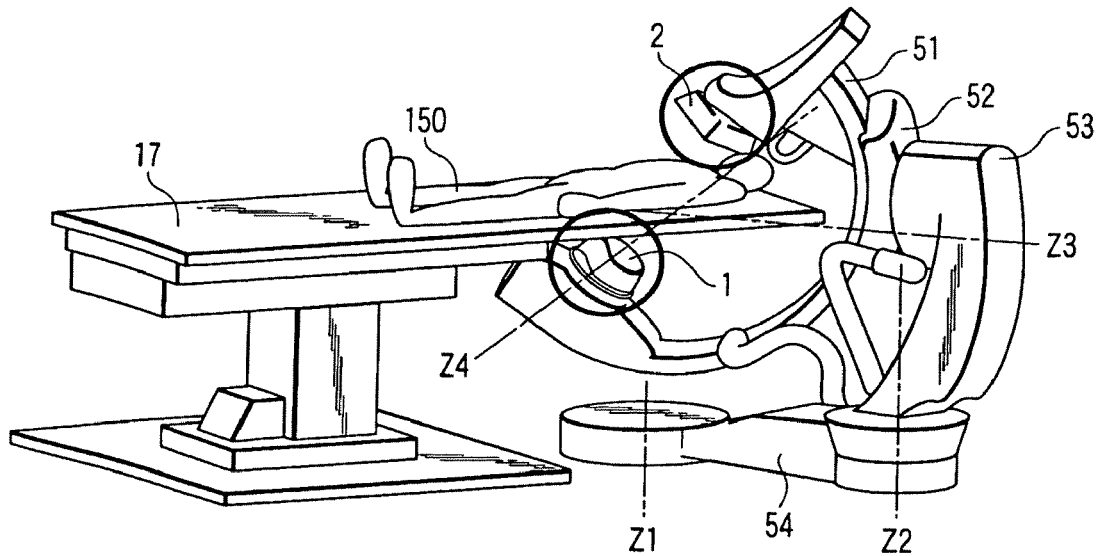
FIG. 8 is a perspective view showing oblique imaging position subjected to posture control by the moving mechanism driving control unit in FIG. 3.
Figure 9:
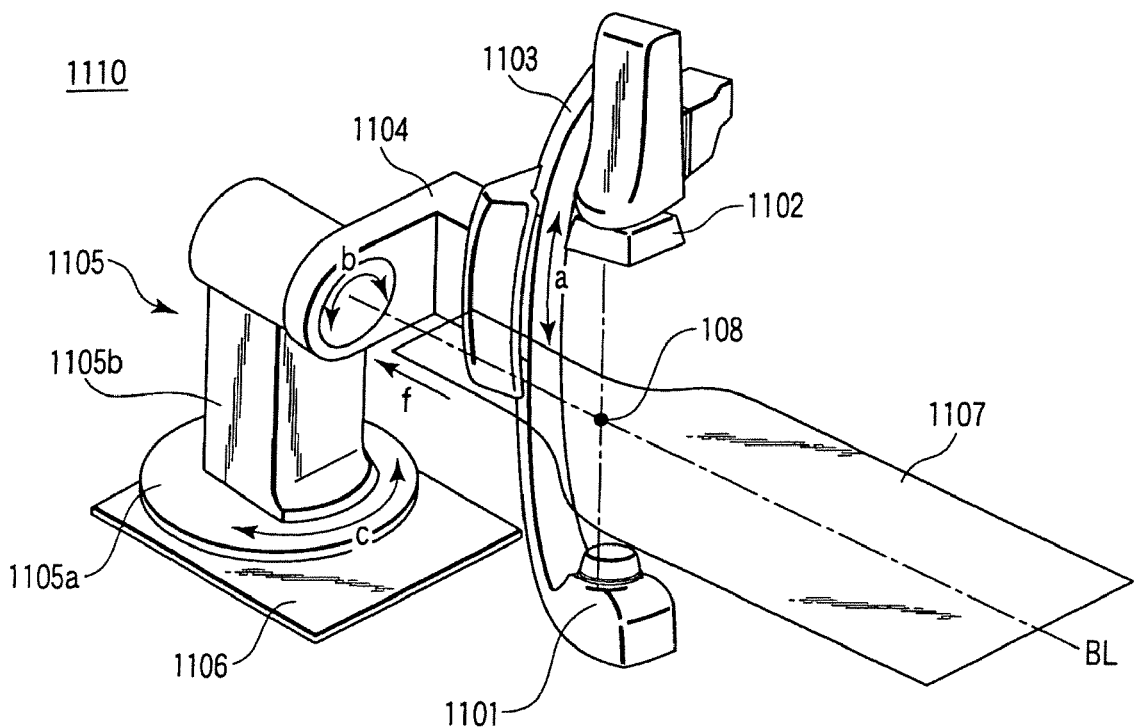
FIG. 9 is a perspective view of a conventional floor type C-arm holding apparatus.

When the oblique position button 232 is clicked or pressed, as shown in FIG. 8, the control unit 33 controls the driving unit 31 to set the C-arm holding apparatus 5 in a posture (position) for oblique position (imaging in an oblique direction between the front surface and a side surface of the subject 150) suitable for inserting the subject 150 into the imaging area from the jugular portion. More specifically, the first posture line PL1 connecting the first rotation axis Z1 to the second rotation axis Z2 coincides with the second posture line PL2 connecting the second rotation axis Z2 to the fifth rotation axis Z5 (imaging axis SA), and the C-arm 51 overlaps above the floor rotating arm 54. The C-arm 51 rotates around the axis Z4 and Z3 by a predetermined angle at a time, and the imaging axis SA intersects the base line BL from an oblique direction. In addition, the X-ray collimating device and the X-ray detecting unit 2 are rotated around the fifth rotation axis Z5 by a predetermined angle, thereby ensuring a direction suitable for an image. When oblique position is to be performed as well, a sufficiently wide work space can be ensured, and a posture which allows the insertion of a subject from the jugular portion side can be set. In addition, since this posture is automatically set by the operation of the position button 232, the C-arm holding apparatus 5 can quickly shift to the posture. The inclination angle is finely adjusted by manually operating the buttons 211 to 218, as needed.

Note that the contents of the functions may be reproduced by assigning them to certain numeral keys of a ten-key pad instead of providing dedicated switches for the buttons 229, 230, 231, and 232.

Control unit 33 rotates the X-ray collimating device and the X-ray detecting unit 2 around the fifth rotation axis Z5 in accordance with arm holder horizontal rotation Z3 and arm slide rotation Z4 when neither the floor rotating nor the stand rotating are 0°. Thereby The direction of the image is prevented being rotated, and the direction of the image is fixed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
a floor rotating arm, one end of the floor rotating arm being mounted on a floor surface so as to be rotatable around a first rotation axis by means of a floor rotating arm rotating mechanism;
a stand mounted on the other end of the floor rotating arm so as to be rotatable around a second rotation axis by means of a stand rotating mechanism;
an arm holder mounted on the stand so as to be rotatable around a third rotation axis by means of a arm holder rotating mechanism;
a C-arm mounted on the arm holder so as to be slidly rotatable around a fourth rotation axis by means of a C-arm sliding mechanism;
an X-ray collimating device of an X-ray generating unit mounted on one end of the C-arm, and an X-ray detecting unit mounted on the other end of the C-arm, the X-ray collimating device and the X-ray detecting unit being rotatable around a fifth rotation axis by means of a axis rotating mechanism;
an operation unit in which operation buttons are arranged; and
a C-arm holding apparatus driving unit which supplies a driving signal to drive the floor rotating arm rotating mechanism, the stand rotating mechanism, the arm holder rotating mechanism, the C-arm sliding mechanism, or the axis rotating mechanism through an angle proportional to an operation time of the operation buttons of the operation unit,
wherein the C-arm holding apparatus driving unit supplies a driving signal to move the fifth rotation axis along a line orthogonal to a longitudinal direction of the subject in accordance with an operation time of a selected button of the operation buttons of the operation unit,
the apparatus further comprising a control unit which controls the C-arm holding apparatus driving unit,
wherein the control unit controls the C-arm holding apparatus driving unit such that the fifth rotation axis moves along the line orthogonal to the longitudinal direction of the subject by interlocking a rotation around the first rotation axis of the floor rotating arm with a rotation around the second rotation axis of the stand.

2. An apparatus according to claim 1, wherein the control unit fixes a direction of an image by interlocking the rotation around the first rotation axis of the floor rotating arm and the rotation around the second rotation axis of the stand with a rotation around the fifth rotation axis of the X-ray collimating device and the X-ray detecting unit.

3. An X-ray diagnostic apparatus, comprising:
a floor rotating arm, one end of the floor rotating arm being mounted on a floor surface so as to be rotatable around a first rotation axis by means of a floor rotating arm rotating mechanism;
a stand mounted on the other end of the floor rotating arm so as to be rotatable around a second rotation axis by means of a stand rotating mechanism;
an arm holder mounted on the stand so as to be rotatable around a third rotation axis by means of a arm holder rotating mechanism;
a C-arm mounted on the arm holder so as to be slidly rotatable around a fourth rotation axis by means of a C-arm sliding mechanism;
an X-ray collimating device of an X-ray generating unit mounted on one end of the C-arm, and an X-ray detecting unit mounted on the other end of the C-arm, the X-ray collimating device and the X-ray detecting unit being rotatable around a fifth rotation axis by means of a axis rotating mechanism;
an operation unit in which operation buttons are arranged; and
a C-arm holding apparatus driving unit which supplies a driving signal to drive the floor rotating arm rotating mechanism, the stand rotating mechanism, the arm holder rotating mechanism, the C-arm sliding mechanism, or the axis rotating mechanism through an angle proportional to an operation time of the operation buttons of the operation unit,
wherein the C-arm holding apparatus driving unit supplies a driving signal to move the fifth rotation axis along a longitudinal direction of the subject, in accordance with an operation time of the operation buttons of the operation unit,
the apparatus further comprising a control unit which controls the C-arm holding apparatus driving unit,
wherein the control unit controls the C-arm holding apparatus driving unit such that the fifth rotation axis moves along a line orthogonal to a longitudinal direction of the subject by interlocking a rotation around the first rotation axis of the floor rotating arm with a rotation around the second rotation axis of the stand.

4. An apparatus according to claim 3, wherein the control unit fixes a direction of an image by interlocking the rotation around the first rotation axis of the floor rotating arm and the rotation around the second rotation axis of the stand with a rotation around the fifth rotation axis of the X-ray collimating device and the X-ray detecting unit.

5. An X-ray diagnostic apparatus, comprising:
a floor rotating arm, one end of the floor rotating arm being mounted on a floor surface so as to be rotatable around a first rotation axis by means of a floor rotating arm rotating mechanism;
a stand mounted on the other end of the floor rotating arm so as to be rotatable around a second rotation axis by means of a stand rotating mechanism;
an arm holder mounted on the stand so as to be rotatable around a third rotation axis by means of a arm holder rotating mechanism;
a C-arm mounted on the arm holder so as to be slidly rotatable around a fourth rotation axis by means of a C-arm sliding mechanism;
an X-ray collimating device of an X-ray generating unit mounted on one end of the C-arm, and an X-ray detecting unit mounted on the other end of the C-arm, the X-ray collimating device and the X-ray detecting unit being rotatable around a fifth rotation axis by means of a axis rotating mechanism;
an operation unit in which operation buttons are arranged;
a C-arm holding apparatus driving unit which supplies a driving signal to drive the floor rotating arm rotating mechanism, the stand rotating mechanism, the arm holder rotating mechanism, the C-arm sliding mechanism, or the axis rotating mechanism through an angle proportional to an operation time of the operation buttons of the operation unit; and
a control unit which controls the C-arm holding apparatus driving unit,
wherein the control unit controls the C-arm holding apparatus driving unit such that the floor rotating arm rotates around the first rotation axis to form a predetermined angle with respect to a base line of the longitudinal direction in accordance with an operation of the operation buttons of the operation unit, in a state where the first rotation axis substantially agrees with the fifth rotation axis.

6. An apparatus according to claim 3, wherein the control unit fixes a direction of an image by interlocking the rotation around the first rotation axis of the floor rotating arm with a rotation around the fifth rotation axis of the X-ray collimating device and the X-ray detecting unit.

7. An apparatus according to claim 5, wherein the predetermined angle is around ±45° with respect to the base line.

8. An apparatus according to claim 5, wherein the predetermined angle is around ±135° with respect to the base line.

9. An X-ray diagnostic apparatus, comprising:
a floor rotating arm, one end of the floor rotating arm being mounted on a floor surface so as to be rotatable around a first rotation axis by means of a floor rotating arm rotating mechanism;
a stand mounted on the other end of the floor rotating arm so as to be rotatable around a second rotation axis by means of a stand rotating mechanism;
an arm holder mounted on the stand so as to be rotatable around a third rotation axis by means of a arm holder rotating mechanism;
a C-arm mounted on the arm holder so as to be slidly rotatable around a fourth rotation axis by means of a C-arm sliding mechanism;
an X-ray collimating device of an X-ray generating unit mounted on one end of the C-arm, and an X-ray detecting unit mounted on the other end of the C-arm, the X-ray collimating device and the X-ray detecting unit being rotatable around a fifth rotation axis by means of a axis rotating mechanism;
an operation unit in which operation buttons are arranged; and
a C-arm holding apparatus driving unit which supplies a driving signal to drive the floor rotating arm rotating mechanism, the stand rotating mechanism, the arm holder rotating mechanism, the C-arm sliding mechanism, or the axis rotating mechanism through an angle proportional to an operation time of the operation buttons of the operation unit; and
a control unit which controls the C-arm holding apparatus driving unit,
wherein the control unit controls the C-arm holding apparatus driving unit such that the floor rotating arm rotates around the third and fifth rotation axes to form a predetermined angle in accordance with an operation of the operation buttons of the operation unit, in a state where the first rotation axis substantially agrees with the fifth rotation axis.

* * * * *